(12) United States Patent
Takahashi et al.

(10) Patent No.: US 10,952,960 B2
(45) Date of Patent: Mar. 23, 2021

(54) BONE REGENERATION AGENT

(71) Applicant: Kao Corporation, Tokyo (JP)

(72) Inventors: Noritaka Takahashi, Tokyo (JP); Akihiko Fujii, Utsunomiya (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 16/487,918

(22) PCT Filed: May 28, 2018

(86) PCT No.: PCT/JP2018/020321
§ 371 (c)(1),
(2) Date: Aug. 22, 2019

(87) PCT Pub. No.: WO2018/221447
PCT Pub. Date: Dec. 6, 2018

(65) Prior Publication Data
US 2019/0380954 A1  Dec. 19, 2019

(30) Foreign Application Priority Data
May 30, 2017 (JP) .............................. JP2017-106613

(51) Int. Cl.
| A61K 31/455 | (2006.01) |
| A61K 9/00 | (2006.01) |
| A61P 1/02 | (2006.01) |
| A61P 19/02 | (2006.01) |
| A61P 19/08 | (2006.01) |
| A23L 33/15 | (2016.01) |

(52) U.S. Cl.
CPC .......... *A61K 9/0063* (2013.01); *A61K 31/455* (2013.01); *A61P 1/02* (2018.01); *A61P 19/02* (2018.01); *A61P 19/08* (2018.01); *A23L 33/15* (2016.08); *A23V 2002/00* (2013.01)

(58) Field of Classification Search
CPC ........ A61K 31/455; A61K 9/0063; A61P 1/02
See application file for complete search history.

(56) References Cited

U.S. PATENT DOCUMENTS

2016/0166528 A1  6/2016  Kim et al.

FOREIGN PATENT DOCUMENTS

| CN | 104324319 A | 2/2015 |
| JP | 61-293909 A | 12/1986 |

OTHER PUBLICATIONS

Filipowska et al. Angiogenesis, Feb. 2017, vol. 20, pp. 291-302.*
International Search Report (ISR) for PCT/JP2018/020321; I.A. fd May 28, 2018, dated Aug. 7, 2018 from the Japan Patent Office, Tokyo, Japan.
International Preliminary Report on Patentability (IPRP), Chapter I of the Patent Cooperation Treaty, including the Written Opinion for PCT/JP2018/020321; I.A. fd May 28, 2018, dated Dec. 3, 2019, by the International Bureau of WIPO, Geneva, Switzerland.
Lee. Y.M. et al., "The role of sirtuin 1 in osteoblastic differentiation in human periodontal ligament cells," J Periodontal Res. Dec. 2011;46(6):712-21. doi: 10.1111/j.1600-0765.2011.01394.x. Epub Jul. 11, 2011.
Li, Y. et al., "Nicotinic acid inhibits vascular inflammation via the SIRT1-dependent signaling pathway," J Nutr Biochem. Nov. 2015;26(11):1338-47. doi: 10.1016/j.jnutbio.2015.07.006. Epub Jul. 26, 2015.
Becks, H. et al., "Comparative study of oral changes in dogs due to deficiencies of pantothenic acid, nicotinic acid, and unknowns of the B vitamin complex," American Journal of Orthodontics and Oral Surgery Apr. 1943;29(4):183-207. doi: 10.1016/S0096-6347(43)90353-9.
Kim, J.-H. et al., "Diabetic characteristics and alveolar bone loss in streptozotocin- and streptozotocin-nicotinamide-treated rats with periodontitis," J Periodontal Res. Dec. 2014;49(6):792-800. doi: 10.1111/jre.12165. Epub Feb. 3, 2014.
The extended European search report including the supplementary European search report and the European search opinion, for EP Appl. No. 18810511.8, dated Dec. 11, 2020, European Patent Office, Munich, Germany.
Park, J-A et al., "Association of Some Vitamins and Minerals with Periodontitis in a Nationally Representative Sample of Korean Young Adults," Biol Trace Elem Res. Aug. 2017;178(2):171-179. doi: 10.1007/s12011-016-0914-x. Epub Dec. 29, 2016. PMID: 28035581.

\* cited by examiner

*Primary Examiner* — Samira J Jean-Louis

(74) *Attorney, Agent, or Firm* — Sterne, Kessler, Goldstein & Fox P.L.L.C.

(57) ABSTRACT

A bone regeneration agent for regenerating a deficient or resorbed bone due to an inflammatory bone resorption disease, containing a niacin compound as an active ingredient.

19 Claims, 1 Drawing Sheet

{Fig. 1}
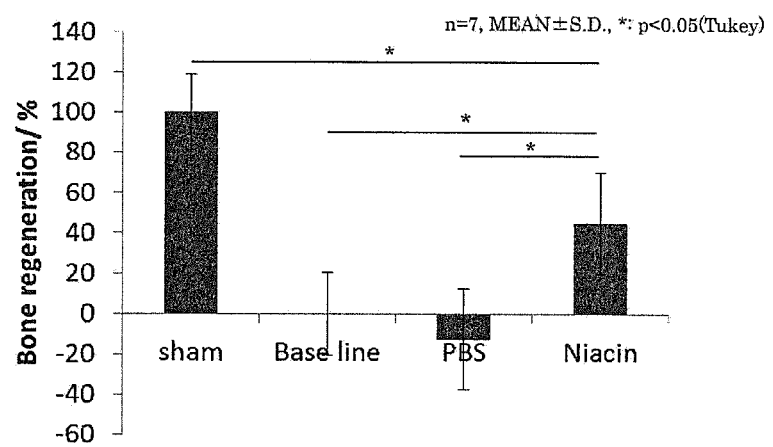
{Fig. 2}
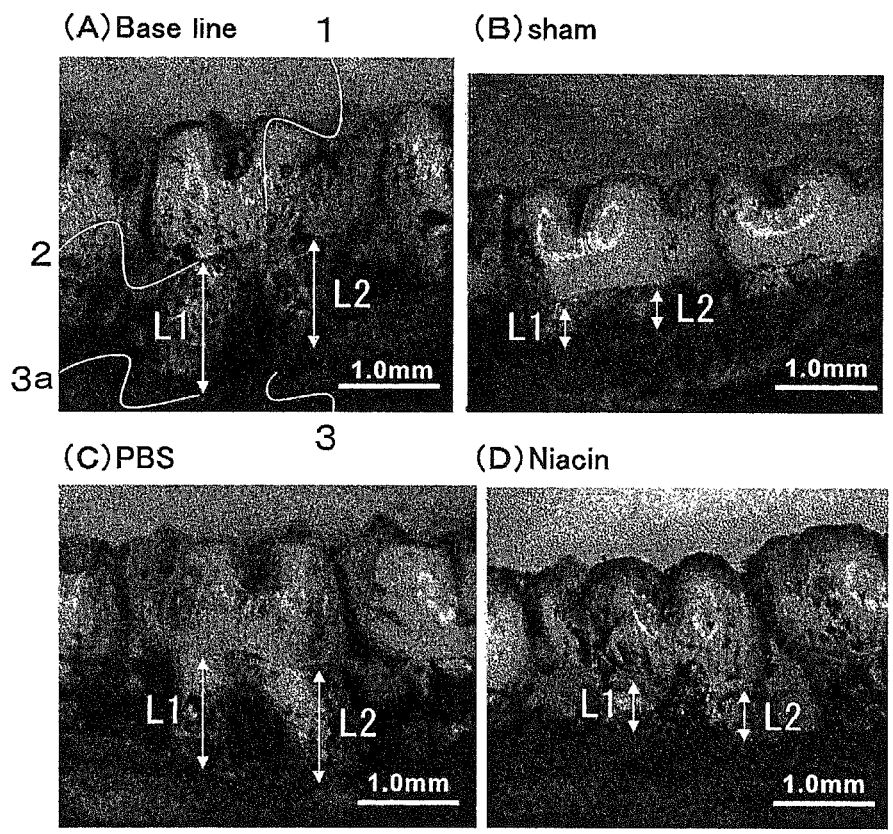

BONE REGENERATION AGENT

TECHNICAL FIELD

The present invention relates to a bone regeneration agent for regenerating a deficient bone or a resorbed bone due to an inflammatory bone resorption disease.

BACKGROUND ART

Super-aged societies have in recent years seen increasing incidence of inflammatory bone resorption diseases, typically periodontitis, rheumatoid arthritis and the like. This is causing elderly people declining quality of life (QOL) and increasing medical expenses for treatment of these diseases.

Periodontal tissue surrounding and helping to support the teeth is composed of gums, periodontal ligament, cementum, and alveolar bone. Among the inflammations of the periodontal tissue, an inflammation localized to the gums is referred to as "gingivitis". In contrast, when the site of inflammation extends beyond the gums, and the periodontal ligament and the alveolar bone are damaged, lost, or resorbed, this is referred to as "periodontitis". These are collectively referred to as "periodontal diseases".

In the case of periodontitis, chronic inflammation occurs in the periodontal tissue due to stimulation by bacterial endotoxins, lipoproteins, and the like in dental plaque, and periodontal pockets are formed in the gingival sulcus. Then, as severity of the periodontitis increases, the alveolar bone is resorbed, damaged, or lost, and eventually, teeth fall out. Recovery from gingivitis is achieved relatively easily by removing dental plaque by appropriate brushing or the like, while recovery from periodontitis is not easily achieved solely by removal of dental plaque. Furthermore, it is considered that since periodontitis exerts various actions on the immune system of the afflicted individual, resorption of the alveolar bone proceeds and the alveolar bone becomes deficient.

In rheumatoid arthritis, disorders occurring in the immune system, whose innate function is to defend against germs and toxins, can lead to inflammation by causing attacks on the individual's own healthy cells or tissues (autoimmune disease). When such inflammation proceeds, cartilages and bones are destroyed, causing pain or joint deformation.

Therapeutic methods for treatment of inflammatory bone resorption diseases such as periodontitis and rheumatoid arthritis include not only surgical methods, but also chemotherapeutic methods of administering an antibiotic for periodontal disease and administering an anti-inflammatory agent for rheumatoid arthritis. Regarding methods for alleviating or treating systemic bone diseases associated with bone resorption, such as osteoporosis, treatment by calcium supplementation, administration of sex hormones, and the like is common. The onset mechanism of inflammatory bone resorption diseases is different from the onset mechanism of bone diseases associated with bone resorption, such as osteoporosis. Therefore, methods for treating these diseases also differ fundamentally from each other. Particularly, resorption or loss of the alveolar bone, which is a characteristic symptom of periodontitis, and destruction of cartilages and bones caused by rheumatoid arthritis are complex biological reactions occurring in localized areas, and many aspects of the processes of onset or progress of the diseases have not yet been clarified. Since the study of methods for treating inflammatory bone resorption diseases can therefore not be effectively pursued only through studies conducted using cultured cells and the like in vitro, studies on drugs and the like are also being conducted in vivo using model animals that develop periodontitis or rheumatic arthritis.

Particularly when periodontitis advances to the point of causing loss or resorption of the alveolar bone, or when cartilage or bone is destroyed due to rheumatoid arthritis, bone regeneration is an effective treatment for inflammatory bone resorption disease.

Patent Literature 1 teaches that an intraoral composition containing niacin (also referred to as nicotinic acid), which is one of water-soluble vitamin B group compounds, or an ester compound thereof, has an effect of promoting blood circulation in the gums. However, Patent Literature 1 is altogether silent regarding concrete examination of the effectiveness of niacin for the regeneration of a deficient or resorbed alveolar bone due to progressing periodontitis.

In addition, a pharmaceutical composition for preventing or treating rheumatoid arthritis, which contains a monoacetyl diacylglycerol compound having a particular structural formula as an active ingredient, is described in Patent Literature 2. However, what is described in Patent Literature 2 is an effect of suppressing inflammation associated with rheumatoid arthritis, and no description is given on the effect of regenerating a cartilage or a deficient or resorbed bone as a result of progressing rheumatoid arthritis.

CITATION LIST

Patent Literatures

Patent Literature 1: JP-A-61-293909 ("JP-A" means unexamined published Japanese patent application)
Patent Literature 2: US 2016/0166528

SUMMARY OF INVENTION

The present invention relates to a bone regeneration agent for regenerating a deficient or resorbed bone due to an inflammatory bone resorption disease, containing a niacin compound as an active ingredient.

Other and further features and advantages of the invention will appear more fully from the following description, appropriately referring to the accompanying drawings.

BRIEF DESCRIPTION OF THE DRAWINGS

FIG. 1 is a graph showing the amount of regeneration of alveolar bone brought by administration of niacin.

FIG. 2(A) is a photograph as a substitute for drawing, showing the state of the alveolar bone in the base line group of Example 1. FIG. 2(B) is a photograph as a substitute for drawing, showing the state of the alveolar bone of the sham group of Example 1. FIG. 2(C) is a photograph as a substitute for drawing, showing the state of the alveolar bone of a rat (PBS group) after being administered with phosphate buffered saline. FIG. 2(D) is a photograph as a substitute for drawing, showing the state of the alveolar bone of a rat (niacin group) after being administered with niacin.

MODE FOR CARRYING OUT THE INVENTION

The present invention relates to the provision of a bone regeneration agent useful as a pharmaceutical product, a quasi-drug, a cosmetic material, or the like, which exhibits an effect of regenerating a deficient or resorbed bone due to an inflammatory bone resorption disease, or is useful as a material or a preparation to be incorporated into these products.

As pointed out above, it is known with regard to periodontitis, one of the inflammatory bone resorption diseases, that niacin or an ester compound thereof promotes blood circulation in the gums. However, there has been no report on the action of these compounds on a deficient or resorbed alveolar bone due to periodontitis.

Against this background, the present inventors conducted a thorough search for a new material exhibiting regeneration action of a deficient or resorbed bone due to an inflammatory bone resorption disease. This investigation led to the discovery of a niacin compound that acts to regenerate a deficient or resorbed bone due to an inflammatory bone resorption disease.

The present invention was completed based on these findings.

The bone regeneration agent of the present invention has an effect of regenerating a deficient or resorbed bone due to an inflammatory bone resorption disease, and is useful as a pharmaceutical product, a quasi-drug, a cosmetic material, or the like, which can exhibit a bone regenerating effect, or is useful as a material or a preparation to be incorporated into these products.

Moreover, the bone regeneration agent of the present invention is used for regenerating a deficient or resorbed bone due to an inflammatory bone resorption disease. In addition, the bone regeneration agent of the present invention contains a niacin compound as an active ingredient. As described in the Examples that follow, when niacin is administered, a deficient or resorbed bone as a result of inflammatory bone resorption disease is regenerated.

Examples of the inflammatory bone resorption disease include periodontitis and rheumatoid arthritis. In the case of periodontal disease, smoking is known to be a risk factor. It is reported that the morbidity rate of periodontal disease is increased 2 to 9 times, as a result of decrease in blood flow in the gums or other tissue caused by smoking (see Guidelines of Examination, Diagnosis, and Treatment Planning for Periodontal Diseases 2008, edited by Japanese Society of Periodontology, Jan. 1, 2009, pp. 1-48). Consistently with this, Patent Literature 1 discloses that periodontal disease is prevented by increasing blood flow using niacin.

On the other hand, it has been reported that blood circulation enhancers such as vitamin E do not improve Gingival index (swelling of gums) or Periodontal probing depth (depth of periodontal pocket, reflecting extent of alveolar bone resorption) (i.e., such enhancers are not effective for amelioration of gingivitis or periodontitis) (see Clin. Prev. Dent., 1991, vol. 13(5), p. 20-24). It is further reported that vitamin E suppresses inflammatory response in a periodontal disease model rat; however, suppression of alveolar bone resorption is not reported (see Arch. Oral Biol., 2013, vol. 58, p. 50-58). And nothing is described or suggested regarding regeneration of a deficient or resorbed alveolar bone. Therefore, it is not appropriate to conclude that improvement of blood flow in the gums is effective for the treatment of periodontitis.

In the current context, "periodontal disease" is a generic term for gingivitis and periodontitis. "Gingivitis" refers to a state in which inflammation has occurred only in the gums and no destruction of periodontal tissue is present. Gingivitis can be completely cured reversibly by removing dental plaque. To the contrary, a state in which inflammation of the gums is accompanied by destruction of periodontal tissue, such as resorption of alveolar bone, is referred to as "periodontitis" or "chronic periodontitis". In periodontitis, destroyed alveolar bone is not generated through the removal of dental plaque only, and regeneration is difficult even by surgery. Therefore, the fact that niacin or an ester compound thereof exhibited an action of promoting blood circulation in the gums does not in itself demonstrate that an effect of regenerating a deficient or resorbed alveolar bone due to an inflammatory bone resorption disease was achieved.

In contrast to this finding, as clarified in the Examples below, the inventors have for the first time demonstrated that niacin compounds exhibit regeneration action of a deficient or resorbed bone due to an inflammatory bone resorption disease.

Examples of the niacin compound used in the present invention include niacin derivatives such as niacin (nicotinic acid), nicotinamide, a nicotinic acid ester, and a nicotinate.

The nicotinic acid ester is preferably an alkyl ester having 1 to 6 carbon atoms of nicotinic acid. Specific examples thereof include methyl nicotinate, ethyl nicotinate, propyl nicotinate, isopropyl nicotinate, n-butyl nicotinate, isobutyl nicotinate, and t-butyl nicotinate.

Examples of the nicotinate include alkaline metal salts, such as sodium salt and potassium salt; alkaline earth metal salts, such as calcium salt and magnesium salt; and basic amino acid salts, such as lysine salt and arginine salt. Among these, niacin, nicotinamide, ethyl nicotinate, and sodium nicotinate are preferable; and niacin is further preferable.

Niacin, which can be preferably used for the present invention, is one of vitamin B compounds and is synthesized from tryptophan, pyridine, or the like. Even if an excessive amount of niacin is administered or ingested, niacin is usually rapidly eliminated from the body via the metabolic system in the body. Therefore, a bone regeneration agent that can be administered for a long time period and is highly safe even when ingested, can be provided by using niacin as an active ingredient.

The niacin compound used in the present invention may be chemically synthesized according to an ordinarily method, or may be obtained by isolation, purification and the like from natural products. Alternatively, a commercially available compound may be used as the niacin compound.

In the present invention, the niacin compound may be used alone in one kind or in combination of two or more kinds thereof.

The above-described active ingredient may be used as a bone regeneration agent. Further, the above-described active ingredient may be used for producing the bone regeneration agent.

The bone regeneration agent of the present invention can be used in the form of an agent composition containing the above-mentioned active ingredient. A form thereof can be appropriately selected. For example, the bone regeneration agent containing the above-described active ingredient and a pharmaceutically acceptable carrier, according to the present invention may be used as the pharmaceutical composition. Furthermore, in a case in which the bone regeneration agent of the present invention is used for the regeneration of a deficient or resorbed alveolar bone due to periodontitis, the bone regeneration agent may be used as a cosmetic composition or a food composition.

When the pharmaceutical composition is prepared, the composition is ordinarily prepared as a preparation containing the above-described active ingredient and preferably a pharmaceutically acceptable carrier. The pharmaceutically acceptable carrier generally means an inert, nontoxic, solid or liquid extender, diluent, encapsulation material or the like that does not react with the above-described active ingredient, and specific examples include a solvent or a dispersion medium such as water, ethanol, polyols, a suitable mixture thereof and vegetable oil.

The form of the pharmaceutical composition can be produced into a solid form, a powdered form, a liquid form, a gel form, or the like according to an ordinarily method, according to the mode of administration.

For example, in a case in which the bone regeneration agent of the present invention is used for the regeneration of a deficient or resorbed alveolar bone due to periodontitis, a mode of administering the bone regeneration agent to the periodontal tissue is preferred. Regarding the mode of administering the bone regeneration agent to the periodontal tissue, a mode of using a topical administration device including a gingival injection part, a gingival sulcus injection part or a gingival sulcus cleaning part for administering the bone regeneration agent of the present invention as a gingival injectable preparation, a gingival sulcus infusion or a gingival sulcus cleaning agent to the periodontal tissue (preferably gingival, and more preferably gingival sulcus), is preferred. By employing such a mode of administration, the bone regeneration agent can be topically administered efficiently to the periodontal tissue, compared to dentrifices and mouthwashes. Here, the gingival injection device, gingival sulcus infusion device or gingival sulcus cleaning device is an injection device, an infusion device or a cleaning device, with which it is easy to administer the bone regeneration agent to a local periodontal region, and various topical administration devices can be employed as long as the devices include an accommodation part that accommodates the bone regeneration agent of the present invention. That is, the bone regeneration agent of the present invention can also be produced into a kit with a topical administration device, or as a container-packed bone regeneration agent.

In the case of preparing a cosmetic composition, the form can be selected as appropriate, and the cosmetic composition can be produced into any arbitrary form such as a solid form, a powdered form, a liquid form, a cream form, a gel form, or the like. Furthermore, the product form of the cosmetic composition is also arbitrarily selected, and examples include dentrifices such as toothpaste, liquid toothpaste, liquid toothpaste, and toothpowder; and oral cosmetics such as mouth rinsing agent, mouthwash, mouth spray, and gum massage cream. In addition, these cosmetics may belong to any of cosmetic products or quasi-drugs, under Japan's law on the securement of product quality, effectiveness, and safety of pharmaceutical products, medical instruments, and the like.

When the food composition is prepared, a form thereof can be appropriately selected. The form includes a general food, and also a health food, a physiologically functional food, a food for sick people, a food for specified health use, and a functional display food. The form also includes a beverage and a feed. A food composition can be used in various formulation forms appropriate for foods or beverages, and examples include fine granules, tablets, granules, powders, capsules, syrups, solutions, and pastes. Specific examples include forms in which the composition stays in the oral cavity for a long time, such as troches, chewable agents, candies, and chewing gums.

The pharmaceutical composition and cosmetic composition described above can be applied in the form of compositions for oral cavity, internally ingested compositions, and the like. Furthermore, the pharmaceutical composition and cosmetic composition may be used for therapeutic purpose, or may be used for non-therapeutic purpose.

The term "non-therapeutic" as used herein is a concept excluding a medical action, that is, treatment action on human bodies by therapy.

In the bone regeneration agent of the present invention, other incorporation components that can be used for pharmaceutical products, quasi-drugs, cosmetic products, or food products may be appropriately incorporated as necessary, to the extent that does not impair the effects of the present invention. For example, a binder, an excipient, an antioxidant, a wetting agent, a flavor, a coloring material, a sweetener, an acidulant, a seasoning, a nonionic surfactant, an anionic surfactant, an oil, an abrasive, a pH adjusting agent, a fluoride, a bactericidal agent, an anti-inflammatory agent, a dental calculus preventing agent, a water-soluble vitamin, a hypersensitivity preventing or alleviating agent, an antiseptic agent, a plant extract, and other efficacious components may be appropriately incorporated as necessary, to the extent that does not impair the effects of the present invention.

The content of the above-described active ingredient in the case of using the bone regeneration agent of the present invention as a composition can be appropriately determined. For example, in the total amount of the composition, the content of the active ingredient in term of niacin is preferably 0.05 mass % or more, more preferably 0.1 mass % or more, and further preferably 0.3 mass % or more. The upper limit thereof is preferably 10 mass % or less, more preferably 5 mass % or less, further preferably 1.5 mass % or less, and particularly preferably 1 mass % or less. Further, the numerical range of the content of the active ingredient is preferably 0.05 to 10 mass %, more preferably 0.1 to 5 mass %, further preferably 0.3 to 1.5 mass %, and particularly preferably 0.3 to 1 mass %.

An administration object of the bone regeneration agent of the present invention is preferably a warm-blooded vertebrate, and more preferably a mammal. Specific examples of the mammal herein include a human and a non-human mammal such as a monkey, a mouse, a rat, a rabbit, a dog, a cat, a bovine, a horse and a pig. The bone regeneration agent of the present invention is preferably administered to a human.

The bone regeneration agent of the present invention can be applied to a subject who desires an effect of regenerating a deficient or resorbed bone due to an inflammatory bone resorption disease, specifically a subject whose bone is deficient or resorbed due to an inflammatory bone resorption disease such as periodontitis or rheumatoid arthritis.

Furthermore, the bone regeneration agent of the present invention can be preferably applied under the conditions in which preferably a periodontal disease, and more preferably periodontitis, has progressed, and the alveolar bone is deficient or resorbed.

When the bone regeneration agent of the present invention is administered to a human or a nonhuman animal, a deficient or resorbed bone due to an inflammatory bone resorption disease, is regenerated.

Thus, in the method of regenerating a bone by using the bone regeneration agent of the present invention, an effective dose of the above-described active ingredient to be applied by administrating the agent can be appropriately determined according to a state of an individual, a body weight thereof, a sex thereof, an age thereof, activity of a material, a pathway of administration, a schedule of administration, a preparation form or other factors.

For example, in the case of applying the present invention to the regeneration of the alveolar bone, the amount of administration of the active ingredient is preferably 3 mg/day or more, and more preferably 18 mg/day or more, in terms of niacin, for one (1) adult (body weight 60 kg). The upper limit thereof is preferably 120 mg/day or less, more preferably 100 mg/day or less, and further preferably 45 mg/day or less. Further, the numerical range of the amount of administration of the active ingredient is preferably 3 to 100 mg/day, and more preferably 18 to 45 mg/day.

The active ingredient can be ingested or administered once a day or divisionally several times a day or during an arbitrary period or at intervals. Furthermore, the administration of the active ingredient may be whole body administration or may be topical administration. In the present invention, the active ingredient is preferably topically administered to the periodontal tissue, more preferably topically administered to the gums, and further preferably topically administered to the gingival sulcus.

Furthermore, the period of administration of the active ingredient for regenerating the alveolar bone varies depending on the extent of damage, loss, or resorption of the alveolar bone and therefore cannot be generally defined. It is preferable to continue administration for a period of time until regeneration of the alveolar bone is completed, and inflammation caused by periodontitis or gingivitis is resolved. Specifically, for example, the period of administration is preferably one (1) week to six (6) years, and more preferably one (1) month to one (1) year.

With regard to the embodiments described above, the present invention also discloses a bone regeneration agent, and a method of using the same and an agent containing the same, described below.

<1> A bone regeneration agent for regenerating a deficient or resorbed bone due to an inflammatory bone resorption disease, containing a niacin compound as an active ingredient.
<2> The bone regeneration agent as described in the above item <1>, wherein the niacin compound is at least one kind of compound selected from the group consisting of niacin, nicotinamide, a nicotinic acid ester (preferably an alkyl ester having 1 to 6 carbon atoms of nicotinic acid, e.g., methyl nicotinate, ethyl nicotinate, propyl nicotinate, isopropyl nicotinate, n-butyl nicotinate, isobutyl nicotinate, and t-butyl nicotinate), and a nicotinate (e.g., an alkaline metal salt, such as sodium salt and potassium salt; an alkaline earth metal salt, such as calcium salt and magnesium salt; and a basic amino acid salt, such as lysine salt and arginine salt); preferably at least one kind of compound selected from the group consisting of niacin, nicotinamide, ethyl nicotinate, and sodium nicotinate; and more preferably niacin.
<3> The bone regeneration agent as described in the above item <1> or <2>, wherein the inflammatory bone resorption disease is periodontitis or rheumatoid arthritis, preferably periodontitis.
<4> The bone regeneration agent as described in the above item <3>, which is used for administering to a periodontal tissue, preferably gingival, more preferably gingival sulcus.
<5> The bone regeneration agent as described in any one of the above items <1> to <4>, which is used as a pharmaceutical composition, a cosmetic composition or a food composition, wherein the content of the active ingredient in term of niacin is 0.05 mass % or more, preferably 0.1 mass % or more, or more preferably 0.3 mass % or more, and 10 mass % or less, preferably 5 mass % or less, more preferably 1.5 mass % or less, or further preferably 1 mass % or less, in the total amount of the composition.
<6> The bone regeneration agent as described in any one of the above items <1> to <5>, wherein the bone that is deficient or resorbed due to an inflammatory bone resorption disease is an alveolar bone.
<7> The bone regeneration agent as described in any one of the above items <1> to <6>, which is administered to a human or a non-human mammal, preferably a human.
<8> Use of a niacin compound as a bone regeneration agent for regenerating a deficient or resorbed bone due to an inflammatory bone resorption disease.
<9> Use of a niacin compound, for producing a bone regeneration agent for regenerating a deficient or resorbed bone due to an inflammatory bone resorption disease.
<10> A method of using a niacin compound, as a bone regeneration agent for regenerating a deficient or resorbed bone due to an inflammatory bone resorption disease.
<11> A method of regenerating a deficient or resorbed bone due to an inflammatory bone resorption disease, containing applying a niacin compound.
<12> The use or method described in any one of the above items <8> to <11>, wherein the niacin compound is at least one kind of compound selected from the group consisting of niacin, nicotinamide, a nicotinic acid ester (preferably an alkyl ester having 1 to 6 carbon atoms of nicotinic acid, e.g., methyl nicotinate, ethyl nicotinate, propyl nicotinate, isopropyl nicotinate, n-butyl nicotinate, isobutyl nicotinate, and t-butyl nicotinate), and a nicotinate (e.g., an alkaline metal salt, such as sodium salt and potassium salt; an alkaline earth metal salt, such as calcium salt and magnesium salt; and a basic amino acid salt, such as lysine salt and arginine salt); preferably at least one kind of compound selected from the group consisting of niacin, nicotinamide, ethyl nicotinate, and sodium nicotinate; and more preferably niacin.
<13> The use or method described in any one of the above items <8> to <12>, wherein the inflammatory bone resorption disease is periodontitis or rheumatoid arthritis, preferably periodontitis.
<14> The use or method described in any one of the above items <8> to <13>, wherein the niacin compound is applied to a subject who desires an effect of regenerating a deficient or resorbed bone due to an inflammatory bone resorption disease, preferably a subject whose bone is deficient or resorbed due to periodontitis or rheumatoid arthritis.
<15> The use or method described in any one of the above items <8> to <14>, wherein the niacin compound is applied under the conditions in which a periodontal disease, preferably periodontitis, has progressed, and an alveolar bone is deficient or resorbed.
<16> The use or method described in the above item <15>, wherein the niacin compound is administered to a periodontal tissue, preferably gingival, more preferably gingival sulcus.
<17> The use or method described in any one of the above items <8> to <16>, wherein the content of the niacin compound in term of niacin is 0.05 mass % or more, preferably 0.1 mass % or more, or more preferably 0.3 mass % or more, and 10 mass % or less, preferably 5 mass % or less, more preferably 1.5 mass % or less, or further preferably 1 mass % or less, in the total amount of the agent.
<18> The use or method described in any one of the above items <8> to <17>, wherein the amount of administration of the niacin compound in terms of niacin for one (1) adult (body weight 60 kg) is 3 mg/day or more, preferably 18 mg/day or more, and 120 mg/day or less, preferably 100 mg/day or less, more preferably 45 mg/day or less.

<19> The use or method described in any one of the above items <8> to <18>, wherein the period of administration of the niacin compound is one (1) week to six (6) years, and preferably one (1) month to one (1) year.

<20> The use or method described in any one of the above items <8> to <19>, wherein the bone that is deficient or resorbed due to an inflammatory bone resorption disease is an alveolar bone.

<21> The use or method described in any one of the above items <8> to <20>, wherein the niacin compound is administered to a human or a non-human mammal, preferably a human.

<22> A niacin compound, to be used for a bone regeneration method for regenerating a deficient or resorbed bone due to an inflammatory bone resorption disease.

<23> Use of a niacin compound, for manufacture of a bone regeneration drug for regenerating a deficient or resorbed bone due to an inflammatory bone resorption disease.

<24> Use of a niacin compound for a non-therapeutic treatment method for bone regeneration for regenerating a deficient or resorbed bone due to an inflammatory bone resorption disease.

<25> The compound or use described in any one of the above items <22> to <23>, wherein the niacin compound is at least one kind of compound selected from the group consisting of niacin, nicotinamide, a nicotinic acid ester (preferably an alkyl ester having 1 to 6 carbon atoms of nicotinic acid, e.g., methyl nicotinate, ethyl nicotinate, propyl nicotinate, isopropyl nicotinate, n-butyl nicotinate, isobutyl nicotinate, and t-butyl nicotinate), and a nicotinate (e.g., an alkaline metal salt, such as sodium salt and potassium salt; an alkaline earth metal salt, such as calcium salt and magnesium salt; and a basic amino acid salt, such as lysine salt and arginine salt); preferably at least one kind of compound selected from the group consisting of niacin, nicotinamide, ethyl nicotinate, and sodium nicotinate; and more preferably niacin.

<26> The compound or use described in any one of the above items <22> to <25>, wherein the inflammatory bone resorption disease is periodontitis or rheumatoid arthritis, preferably periodontitis.

<27> The compound or use described in any one of the above items <22> to <26>, wherein the niacin compound is applied to a subject who desires an effect of regenerating a deficient or resorbed bone due to an inflammatory bone resorption disease, preferably a subject whose bone is deficient or resorbed due to periodontitis or rheumatoid arthritis.

<28> The compound or use described in any one of the above items <22> to <27>, wherein the niacin compound is applied under the conditions in which a periodontal disease, preferably periodontitis, has progressed, and an alveolar bone is deficient or resorbed.

<29> The compound or use described in the above item <28>, wherein the niacin compound is administered to a periodontal tissue, preferably gingival, more preferably gingival sulcus.

<30> The compound or use described in any one of the above items <22> to <29>, wherein the niacin compound is applied in the form of a pharmaceutical composition.

<31> The compound or use described in any one of the above items <22> to <29>, wherein the niacin compound is applied in the form of a cosmetic composition.

<32> The compound or use described in any one of the above items <22> to <29>, wherein the niacin compound is applied in the form of a food composition.

<33> The compound or use described in any one of the above items <30> to <32>, wherein the content of the niacin compound in term of niacin is 0.05 mass % or more, preferably 0.1 mass % or more, or more preferably 0.3 mass % or more, and 10 mass % or less, preferably 5 mass % or less, more preferably 1.5 mass % or less, or further preferably 1 mass % or less, in the total amount of the composition.

<34> The compound or use described in any one of the above items <22> to <33>, wherein the amount of administration of the niacin compound in terms of niacin for one (1) adult (body weight 60 kg) is 3 mg/day or more, preferably 18 mg/day or more, and 120 mg/day or less, preferably 100 mg/day or less, more preferably 45 mg/day or less.

<35> The compound or use described in any one of the above items <22> to <34>, wherein the period of administration of the niacin compound is one (1) week to six (6) years, and preferably one (1) month to one (1) year.

<36> The compound or use described in any one of the above items <22> to <35>, wherein the bone that is deficient or resorbed due to an inflammatory bone resorption disease is an alveolar bone.

<37> The compound or use described in any one of the above items <22> to <36>, wherein the niacin compound is administered to a human or a non-human mammal, preferably a human.

<38> A method for non-therapeutically regenerating a deficient or resorbed bone due to an inflammatory bone resorption disease, containing applying a niacin compound.

<39> The method described in the above item <38>, wherein the niacin compound is at least one kind of compound selected from the group consisting of niacin, nicotinamide, a nicotinic acid ester (preferably an alkyl ester having 1 to 6 carbon atoms of nicotinic acid, e.g., methyl nicotinate, ethyl nicotinate, propyl nicotinate, isopropyl nicotinate, n-butyl nicotinate, isobutyl nicotinate, and t-butyl nicotinate), and a nicotinate (e.g., an alkaline metal salt, such as sodium salt and potassium salt; an alkaline earth metal salt, such as calcium salt and magnesium salt; and a basic amino acid salt, such as lysine salt and arginine salt); preferably at least one kind of compound selected from the group consisting of niacin, nicotinamide, ethyl nicotinate, and sodium nicotinate; and more preferably niacin.

<40> The method described in the above item <38> or <39>, wherein the inflammatory bone resorption disease is periodontitis or rheumatoid arthritis, preferably periodontitis.

<41> The method described in any one of the above items <38> to <40>, wherein the niacin compound is applied to a subject who desires an effect of regenerating a deficient or resorbed bone due to an inflammatory bone resorption disease, preferably a subject whose bone is deficient or resorbed due to periodontitis or rheumatoid arthritis.

<42> The method described in any one of the above items <38> to <41>, wherein the niacin compound is applied under the conditions in which a periodontal disease, preferably periodontitis, has progressed, and an alveolar bone is deficient or resorbed.

<43> The method described in the above item <42>, wherein the niacin compound is administered to a periodontal tissue, preferably gingival, more preferably gingival sulcus.

<44> The method described in any one of the above items <38> to <43>, wherein the amount of administration of the niacin compound in terms of niacin for one (1) adult (body weight 60 kg) is 3 mg/day or more, preferably 18 mg/day or more, and 120 mg/day or less, preferably 100 mg/day or less, more preferably 45 mg/day or less.

<45> The method described in any one of the above items <38> to <44>, wherein the period of administration of the niacin compound is one (1) week to six (6) years, and preferably one (1) month to one (1) year.

<46> The method described in any one of the above items <38> to <45>, wherein the bone that is deficient or resorbed due to an inflammatory bone resorption disease is an alveolar bone.

<47> The method described in any one of the above items <38> to <46>, wherein the niacin compound is administered to a human or a non-human mammal, preferably a human.

<48> A cosmetic composition for regenerating a deficient or resorbed bone due to an inflammatory bone resorption disease, containing a niacin compound as an active ingredient.

<49> A food composition for regenerating a deficient or resorbed bone due to an inflammatory bone resorption disease, containing a niacin compound as an active ingredient.

<50> The composition described in the above item <48> or <49>, wherein the niacin compound is at least one kind of compound selected from the group consisting of niacin, nicotinamide, a nicotinic acid ester (preferably an alkyl ester having 1 to 6 carbon atoms of nicotinic acid, e.g., methyl nicotinate, ethyl nicotinate, propyl nicotinate, isopropyl nicotinate, n-butyl nicotinate, isobutyl nicotinate, and t-butyl nicotinate), and a nicotinate (e.g., an alkaline metal salt, such as sodium salt and potassium salt; an alkaline earth metal salt, such as calcium salt and magnesium salt; and a basic amino acid salt, such as lysine salt and arginine salt); preferably at least one kind of compound selected from the group consisting of niacin, nicotinamide, ethyl nicotinate, and sodium nicotinate; and more preferably niacin.

<51> The composition described in any one of the above items <48> to <50>, wherein the inflammatory bone resorption disease is periodontitis or rheumatoid arthritis, preferably periodontitis.

<52> The composition described in any one of the above items <48> to <51>, wherein the content of the niacin compound in term of niacin is 0.05 mass % or more, preferably 0.1 mass % or more, or more preferably 0.3 mass % or more, and 10 mass % or less, preferably 5 mass % or less, more preferably 1.5 mass % or less, or further preferably 1 mass % or less, in the total amount of the composition.

<53> The composition described in any one of the above items <48> to <52>, wherein the bone that is deficient or resorbed due to an inflammatory bone resorption disease is an alveolar bone.

<54> The composition described in any one of the above items <48> to <53>, which is administered to a human or a non-human mammal, preferably a human.

EXAMPLES

Hereinafter, the present invention will be described more in detail with reference to Examples, but the present invention is not limited thereto.

Example 1 Test for Regenerating Alveolar Bone of Rat (1) Method for Accelerating Loss or Resorption of Alveolar Bone Twenty-eight 8-week-old male Wister Rats were purchased from Japan SLC, Inc., and the rats were acclimated for one week. Subsequently, the body weights of the rats were measured, and the rats were assigned into four groups (base line group, Sham group, PBS group, and niacin group) such that the average body weights of the groups would be even.

Under isoflurane inhalation anesthesia, No. 3-0 nylon sutures (manufactured by Akiyama Seisakusho Co., Ltd.) were ligated to the right and left second molars in the upper jaw of the rats of the base line group, PBS group, and niacin group to induce periodontitis, and the rats of the respective groups were reared for two weeks. Meanwhile, ligation was not performed for the rats of the sham group.

After rearing for two weeks, the ligatures (No. 3-0 nylon sutures described above) were excised from the rats of the PBS group and the niacin group. For the base line group, the rats were euthanized by bleeding from the abdominal aorta under isoflurane inhalation anesthesia, and the alveolar bone resorption depths of the respective groups were measured by the following method.

(2) Administration of Alveolar Bone Regeneration Agent

A solution (25 mM) of niacin (manufactured by Wako Pure Chemical Industries, Ltd.) in phosphate buffered saline (hereinafter, referred to as "PBS"; manufactured by Gibco, Inc.) was prepared. Then, under isoflurane inhalation anesthesia, 100 µL of the niacin solution thus prepared was dropped onto the right and left second molars of the rats of the niacin group for 4 weeks twice a day (9:30 and 16:00 daily).

For the rats of the sham group and PBS group, PBS was dropped, instead of the niacin solution, onto the right and left second molars, similarly to the rats of the niacin group.

(3) Measurement of Alveolar Bone Regeneration Amount

The respective drugs were administered for 4 weeks, and then the rats were euthanized under isoflurane inhalation anesthesia by bleeding from the abdominal aorta.

The maxillary tissues were collected from the rats so as to include all molars, soft tissues were completely removed, and then the maxillary tissues were stained with Methylene Blue. Then, at two sites of the root portions of the second molar 1 where a ligature was ligated, the length from the Cement-Enamel junction 2 to the alveolar bone crest 3a of the alveolar bone 3 was measured (L1, L2; see the arrows in FIGS. 2(A) to 2(D)), and the sum of the lengths measured at the two sites (L1+L2) was calculated as the alveolar bone resorption depth. Meanwhile, the alveolar bone crest 3a was identified by visual inspection from photographs.

The alveolar bone regeneration amount of the base line group was designated as 0%, and the alveolar bone regeneration amount of the Sham group was designated as 100%. Thus, the alveolar bone regeneration amounts of the PBS group and the niacin group were calculated from the average alveolar bone resorption depth thus calculated. The results are shown in FIG. 1. Here, for a comparison of the various groups, a statistical analysis was performed using Tukey's method, and the significance level was set to 5%.

As shown in FIG. 1, the regeneration amount of the alveolar bone significantly increased in the rats of the niacin group, compared to the rats of the PBS group.

As shown in the Examples described above, when a niacin compound is applied, a deficient or resorbed bone due to an inflammatory bone resorption disease is significantly regenerated.

Therefore, the bone regeneration agent of the present invention containing a niacin compound as an active ingredient has an action of regenerating a deficient or resorbed bone due to an inflammatory bone resorption disease, and is useful as a pharmaceutical product, a quasi-drug, a cosmetic material, a food product, or the like, which can exhibit an effect of regenerating a deficient or resorbed bone due to an inflammatory bone resorption disease, or as a material or a preparation to be incorporated into these products.

Having described our invention as related to the present embodiments, it is our intention that the invention not be limited by any of the details of the description, unless otherwise specified, but rather be construed broadly within its spirit and scope as set out in the accompanying claims.

This application claims priority on Patent Application No. 2017-106613 filed in Japan on May 30, 2017, which is entirely herein incorporated by reference.

REFERENCE SIGNS LIST

1 Second molar
2 Cement-Enamel junction
3 Alveolar bone
3a Alveolar bone crest
L1 Length from Cement-Enamel junction to alveolar bone crest
L2 Length from Cement-Enamel junction to alveolar bone crest

What is claimed is:

1. A method of regenerating alveolar bone in a subject in which alveolar bone has been damaged, lost or resorbed due to periodontitis, comprising
  applying, to periodontal tissue at the periodontitis site,
  a composition that comprises an effective dose of at least one niacin compound selected from the group consisting of niacin and a nicotinate,
  for a period of time effective to regenerate alveolar bone at the periodontitis site.

2. The method of claim 1, wherein the niacin compound is at least one compound selected from the group consisting of niacin, and sodium nicotinate.

3. The method of claim 1, wherein the composition is applied to the subject's gums.

4. The method of claim 1, wherein the composition comprises the niacin compound in an amount that is 0.05 mass % or more in terms of niacin.

5. The method of claim 1, wherein the composition is applied to the subject's gingival sulcus.

6. The method of claim 1, wherein the subject's alveolar bone at the periodontitis site has been resorbed.

7. The method of claim 1, wherein the composition is administered to a human.

8. The method of claim 1, wherein the niacin compound is niacin.

9. The method of claim 4, wherein the composition comprises the niacin compound in an amount that is 0.05 mass % or more and 10 mass % or less, in terms of niacin.

10. The method of claim 9, wherein the composition comprises the niacin compound in an amount that is 0.1 mass % or more and 5 mass % or less, in terms of niacin.

11. The method of claim 1, wherein the composition comprises a pharmaceutically acceptable carrier.

12. The method of claim 1, wherein the subject's alveolar bone has been damaged at the periodontitis site.

13. The method of claim 1, wherein the subject's alveolar bone has been lost at the periodontitis site.

14. The method of claim 1, wherein the composition is a liquid or a gel.

15. The method of claim 1, wherein the composition is administered to the subject's gingival tissue.

16. The method of claim 1, wherein the subject is administered a dose, in terms of niacin, of 3 mg/day or more and 100 mg/day or less per 60 kg.

17. The method of claim 16, wherein the dose in terms of niacin is 18 mg/day or more and 45 mg/day or less per 60 kg.

18. The method of claim 1, wherein the composition is administered for one week to six years.

19. The method of claim 18, wherein the composition is administered for one month to one year.

* * * * *